United States Patent [19] [11] 4,145,357
Ochi et al. [45] Mar. 20, 1979

[54] STEROID DERIVATIVES AND PROCESS FOR PREPARING THE SAME

[75] Inventors: Kiyoshige Ochi, Kawagoe; Isao Matsunaga; Minoru Shindo, both of Tokyo; Chikara Kaneko, Kanazawa, all of Japan

[73] Assignee: Chugai Syiyaku Kabushiki Kaisha, Tokyo, Japan

[21] Appl. No.: 855,362

[22] Filed: Nov. 28, 1977

[30] Foreign Application Priority Data

Dec. 8, 1976 [JP] Japan ................ 51-146571

[51] Int. Cl.² .................................. C07J 9/00
[52] U.S. Cl. .................. 260/397.2; 260/239.55 R
[58] Field of Search ............ 260/397.2, 239.55 R; /Machine Searched Steroids

[56] References Cited

U.S. PATENT DOCUMENTS

| 2,705,232 | 3/1955 | Dodson | 260/397.2 |
| 3,152,152 | 10/1964 | Wechter | 260/397.2 |
| 3,822,254 | 7/1974 | Partridge et al. | 260/397.2 |
| 3,856,780 | 12/1974 | Narwid et al. | 260/397.2 |
| 3,929,770 | 12/1975 | Ishikawa et al. | 260/397.2 |
| 3,959,320 | 5/1976 | Salmond | 260/397.2 |
| 3,976,636 | 8/1976 | Salmond | 260/397.2 |
| 3,994,878 | 11/1976 | Partridge, Jr. et al. | 260/239.55 |

OTHER PUBLICATIONS

"Steroids", Jan. 1978, pp. 99–102.
"Steroids", (1978), article by Batta et al., p. 102.

*Primary Examiner*—Elbert L. Roberts
*Attorney, Agent, or Firm*—Browdy and Neimark

[57] ABSTRACT

A steroid derivative represented by the formula

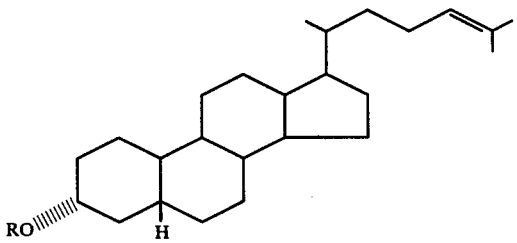

wherein R is as defined hereunder and a process for preparing the same are disclosed. The derivative is an intermediate for the production of various useful compounds.

14 Claims, No Drawings

STEROID DERIVATIVES AND PROCESS FOR PREPARING THE SAME

BACKGROUND OF THE INVENTION

This invention relates to a steroid derivative represented by the formula

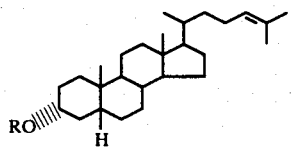

wherein R is hydrogen, acyl, triarylmethyl, methoxymethyl, tetrahydropyranyl or benzyl and also relates to a process for preparing the derivative.

In recent years, extensive research has been carried on for developing vitamin D compounds which have biologically high activities. Especially, steroid compounds having hydroxyl group(s) attached to their side chains, particularly, cholesterol compounds having hydroxyl group(s) at 24 and/or 25 positions, have attracted researchers' attention as an intermediate for the production of active vitamin $D_3$ compounds. Fucosterol, desmosterol or the like is thought to be a possible starting compound for the production of such intermediate, but they are hardly available natural substances, and therefore, it is almost impossible to commercially supply them as raw materials.

On the other hand, according to a process for preparing the vitamin $D_3$ compounds described in, for example, Japanese Patent Disclosures Nos. 18458/1975, 35152/1975, 56444/1976 and 70759/1976, the vitamin $D_3$ compound, for example, 1α,25-dihydroxycholecalciferol is prepared from as a starting compound, a 3-hydroxy-5-ene-steroid derivative, i.e. cholesterol derivative. However, in these processes, protection of the hydroxyl group at 3-position and the double bond at 5-position of the steroid derivative is essential for the production of 25-hydroxycholesterol, because 25-hydroxycholesterol is a key intermediate indispensable to prepare 1α,25-dihydroxycholecalciferol and introduction of a hydroxyl group into 25-position of the steroid derivative is necessary to prepare such intermediate. Such protection requires a combination of many types of reactions and complicated operation, and gives the processes many commercial disadvantages.

The inventors of this invention carefully studied the problems of the prior art and, after intensive research found that lithocholic acid, which is easily available, can be used to prepare the compound represented by the formula above with only several steps of reactions. Further, using the thus prepared compound as an intermediate, they succeeded in easily preparing various useful compounds to complete the invention.

DETAILED DESCRIPTION OF THE INVENTION

The compound represented by the formula (I) may be prepared by, for example, reacting an acid or a halogenating agent with a compound represented by the formula

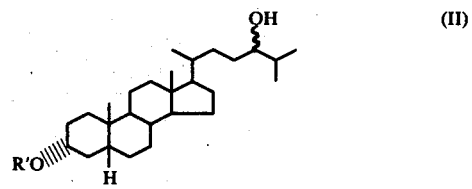

wherein R' is acyl, triarylmethyl, methoxymethyl, tetrahydropyranyl or benzyl to dehydrate the compound and then, optionally hydrolizing the product.

The compound represented by the formula (II) may be prepared by, for example, reacting acetyllithocholyl chloride disclosed in U.S. Pat. No. 2,705,232 with isopropyl magnesium halide, isopropylzinc or isopropylcadmium in an inert solvent such as benzene, toluene, diethyl ether or the like and reducing the product with an alkali metal borohydride such as potassium borohydride, sodium borohydride or the like.

In order to practice the method of this invention, an acid or a halogenating agent is used. In case the acid is used, the compound (II) may be reacted with the acid in the absence of or in the presence of a solvent such as benzene, xylene, dimethylformamide, toluene, isopropyl alcohol or amyl alcohol at a temperature of from room temperature to 200° C. for 1–24 hours to give the object compound represented by the formula (I) above in a high yield. The acids which may be used in this method include sulfuric acid, p-toluenesulfonic acid, phosphoric anhydride and the like.

On the other hand, in case the halogenating agent is used, the compound (II) may be reacted with the agent in a basic solvent such as pyridine, triethylamine, dimethylaniline, picoline or the like or in a neutral solvent such as benzene, chloroform, dichloromethane or the like at a temperature of from room temperature to 200° C. for ½ to 24 hours to give the object compound (I). The halogenating agents which are useful in the method of this invention include phosphorus oxychloride, thionyl chloride, phosphorus pentachloride, phosphorus trichloride and the like. If a neutral solvent is used, the reaction may be preferably carried out in the presence of an agent for de-hydrogen halide such as an inorganic base, for example, potassium hydroxide, sodium hydroxide or the like or an alkaline organic compound such as pyridine, triethylamine, collidine, dimethylaniline, picoline or the like.

The thus obtained compound (I) has protective group attached to hydroxyl group at 3-position. If desired, the protective group may be removed by hydrolysis in a conventional manner to give 3α-hydroxy-5β-cholest-24-ene. The hydrolysis may be easily effected by adding an alkali such as potassium hydroxide or sodium hydroxide to a reaction mixture containing the compound (I) and subjecting the system to reaction at room temperature for several hours.

With the use of compound (I), several useful compounds may be prepared as described hereunder.

A-1: Preparation of 3α,25-Dihydroxy-5β-cholestane

3α,25-Dihydroxy-5β-cholestane is prepared by reacting a mercuric salt of a strong organic acid with 3α-hydroxy-5β-cholest-24-ene to introduce mercury oxy group and then reducing the product with an alkali metal borohydride.

The preferred mercuric salt of strong organic acid is mercuric trifluoroacetate. The reduction may be easily carried out under alkaline conditions which are accomplished by, for example, adding sodium hydroxide or potassium hydroxide to the reaction mixture, by adding a reducing agent such as alkali metal borohydride, more specifically potassium borohydride, sodium borohydride or the like. The reaction is completed within a short period of time to yield the object compound, 3α,25-dihydroxy-5β-cholestane.

A-2: Preparation of 3α,25-Dihydroxy-5β-cholestane

3α,25-Dihydroxy-5β-cholestane may be prepared by reacting a peroxide with 3α-hydroxy-5β-cholest-24-ene and reducing the resulting 3α-hydroxy-24,25-epoxy-5β-cholestane with a metal hydride.

Peroxides preferably used in this reaction include organic peroxides, such as an aromatic peracids, for example, perbenzoic acid, m-chloroperbenzoic acid and the like and aliphatic peracids, such as permaleic acid, peracetic acid and trifluoroperacetic acid. The reaction is carried out in a suitable solvent such as chloroform by cooling or heating or at room temperature, depending upon the properties of solvent used.

Metal hydrides preferred for the reduction of the 24,25-epoxide include lithium aluminium hydride, lithium borohydride or the like. The reduction is carried out in an ether such as diethyl ether, tetrahydrofuran or 1,2-dimethoxyethane at a temperature of from room temperature to refluxing temperature.

A-3: Preparation of 1α,25-Dihydroxycholecalciferol

25-Hydroxy-cholesta-1,4,6-trien-3-one may be prepared by the method described in Japanese Patent Disclosure No. 36654/1977 (Japanese Patent Application No. 112078/1975). That is, 3α,25-dihydroxy-5β-cholestane is treated with 2,3-dichloro-5,6-dicyanobenzoquinone and the resulting 25-hydroxy-cholesta-1,4-dien-3-one is reacted with chloranil in the presence of 2,3-dichloro-5,6-dicyanohydroquinone to give 25-hydroxy-cholesta-1,4,6-trien-3-one. The product is subsequently treated in a conventional manner such as one of those described in Japanese Patent Disclosures Nos. 84555/1975 and 84560/1975 to easily give 1α,25-dihydroxycholecalciferol.

B-1: Preparation of 3α,24,25-trihydroxy-5β-cholestane

3α,24,25-Trihydroxy-5β-cholestane may be prepared by reacting a peroxide with 3α-hydroxy-5β-cholest-24-ene and treating the resulting 24,25-epoxy compound with an acid.

Peroxides which may be used in this reaction include hydrogen peroxide, performic acid, peracetic acid, perbenzoic acid, and m-chloroperbenzoic acid. Although the peroxide and the acid may be used separately, an acid-peroxide system such as formic acid-hydrogen peroxide may be used whereby decomposition of the epoxy compound occurs simultaneously with oxidation to give a 24-formyloxy-25-hydroxy compound. The compound may be easily converted to the corresponding 24,25-dihydroxy compound by means of a conventional treatment with an alkali.

B-2: Preparation of 3α,24,25-Trihydroxy-5β-cholestane

Instead of using the method of B-1 above, the 24,25-dihydroxy compound may be prepared by reacting 3α-hydroxy-5β-cholest-24-ene with osmium tetraoxide to give the corresponding osmate and decomposing the ester to give 24,25-dihydroxy compound.

The oxidation with osmium tetraoxide is effected in the presence of a solvent. Although diethyl ether, benzene, dioxane, chloroform, carbon tetrachloride, ethyl acetate and a mixture thereof may be used as a suitable solvent, diethyl ether and benzene are preferable. The reaction temperature and reaction time are not critical for this process, but, the reaction is preferably carried out at room temperature or below, preferably at room temperature, for a period ranging from several hours to several days. The oxidation gives an osmate of a starting steroid compound which contains osmium tetraoxide, attached to double bond at 24-position of the steroid compound. The osmate compound may be decomposed by an agent such as pyridine-aqueous solution of alkali bisulfite, ethanol-aqueous solution of alkali bisulfite, zinc-acetic acid, zinc-concentrated hydrochloric acid, potassium chlorate-sulfuric acid, chromic acid-acetic acid, formaldehyde-aqueous solution of alkali hydroxide, hydrogen sulfide or the like.

B-3: Preparation of 3α,24,25-Trihydroxycholecalciferol

3α,24,25-Trihydroxy-5β-cholestane which can be prepared by a method described in B-1 or B-2 above may be converted into the 3α,24,25-trihydroxycholecalciferol in a manner as in A-3 above.

EXAMPLE 1

Metallic magnesium flakes (7.27 g) were suspended in dry diethyl ether (200 ml) and to the suspension was added dropwise a solution of isopropyl bromide (28.1 ml) in dry diethyl ether (100 ml) while stirring at room temperature. The mixture was refluxed for 30 minutes to completely dissolve the magnesium flakes. After cooling, anhydrous cadmium bromide was slowly added to the solution and the solution was refluxed for one hour. After addition of dry benzene, most of the diethyl ether was evaporated.

Separately, acetyllithocholyl chloride was prepared by dissolving acetyllithocholic acid (10 g) in thionyl chloride (100 ml), allowing the solution to stand for 2 hours at room temperature and distilling to remove unreacted thionyl chloride under reduced pressure. The resulting acetyllithocholic acid chloride was dissolved in dry benzene and the solution was added dropwise to the previously prepared solution of isopropylcadmium in benzene while vigorously stirring at a temperature ranging from 5° to 7° C. Five to ten minutes after completion of the addition, cold water and 5% hydrochloric acid were added to the solution followed by adding fresh benzene. The benzene layer was separated, washed with water and dried over magnesium sulfate, and evaporated. The residue was purified by chromatography to give 5 g of 3α-hydroxy-5β-cholestan-24-one acetate having a melting point of 96°–98° C.

EXAMPLE 2

3α-Hydroxy-5β-cholestan-24-one acetate prepared as in Example 1 (852.9 g) was dissolved in diethyl ether (20 ml). The solution was added dropwise over 10 minutes to a solution of calcium borohydride which had been prepared from calcium chloride (808 mg), methanol (20 ml) and sodium borohydride (424 mg) and stirred for one hour at −10° C. One hour after completion of the addition, excess calcium borohydride was decomposed by the addition of aqueous acetic acid and the mixture was extracted with ethyl acetate. The ethyl acetate layer was washed with water and dried over anhydrous sodium sulfate and evaporated to give 701.7 mg of 3α,24-dihydroxy-5β-cholestane 3-acetate as oil.

I.R. spectrum (cm$^{-1}$, KBr): 3450(OH), 1737 (CO of acetyl radical).

N.M.R. spectrum (δ in CDCl$_3$): 0.64(3H,S), 0.87(3H,S), 0.93(3H,S), 0.96(3H,S), 2.02(3H,S), 3.30(1H,m) 4.65(1H,m).

EXAMPLE 3

(a) 3α,24-Dihydroxyss-5β-cholestane 3-acetate (701.7 mg) prepared according to Example 2 was dissolved in pyridine (10 ml) and to the solution was added phosphorus oxychloride (1.5 ml). The mixture was left standing overnight. The reaction mixture was poured into ice water and the resulting oil was extracted with diethyl ether. The ether layer was washed with water, dried over anhydrous sodium sulfate and evaporated to give 3α-hydroxy-5β-cholest-24-ene acetate as oil.

I.R. spectrum (film, cm$^{-1}$): 1735 (CO of acetyl radical).

N.M.R. spectrum (δ in CDCl$_3$): 0.64(3H,s), 0.92(6H,S) 1.58(3H,S), 1.68(3H,S) 2.02(3H,S), 4.5–5.3(2H,m).

Mass spectrum (m/e): 428(M$^+$), 413, 368, 353, 344, 315, 285, 255, 215.

(b) To the oil was added a solution of potassium hyroxide (1 g) in methanol (30 ml) and the mixture was allowed to stand at room temperature for 3 hours. The reaction mixture was extracted with diethyl ether and the extract was washed with water, dried and evaporated. The residue was recrystallized from hexane to give 489.3 mg of 3α-hydroxy-5β-cholest-24-ene having a melting point of 117°–118° C.

I.R. spectrum (cm$^{-1}$, KBr): 3325(OH). N.M.R. spectrum (δ in CDCl$_3$): 0.62(3H,S), 0.91(6H,S), 1.57(3H,S), 1.66(3H,S), 3.7(2H,m), 5.1(1H,m).

Mass spectrum (m/e): 386(M$^+$), 368, 271, 253, 285, 273, 255, 215.

EXAMPLE 4

3α-Hydroxy-5β-cholest-24-ene (130.1 mg) was dissolved in the mixture of water (0.5 ml), tetrahydrofuran (1 ml) and dimethylformamdie (1 ml) and to the solution was added mercuric trifluroacetate (215.4 mg). The mixture was stirred room temperature for 7 hours. To the reaction mixture were added 3N aqueous sodium hydroxide solution (1 ml) and then a solution of 100 mg of sodium borohydride in 1 ml of 3N aqueous sodium hydroxide solution followed by stirring the mixture for one hour. The reaction mixture was extracted with diethyl ether, and the extract was washed with diluted hydrochloric acid and then with water, dried over anhydrous sodium sulfate and evaporated. The oily residue was chromatographed on silica gel (10 g) to give 53.7 mg of purified 3α,25-hydroxy-5β-cholestane. After crystallization from ethanol, the produce had a melting point of 184°–185° C.

I.R. spectrum (cm$^{-1}$, KBr): 3340(OH).

N.M.R. spectrum (δ in CDCl$_3$): 0.62(3H,S), 0.89(6H,S), 1.17(6H,S), 3.6(1H,m).

Mass spectrum (m/e): 404(M$^+$) 386.

EXAMPLE 5

3α-Hydroxy-5β-cholest-24-ene (161.5 mg) was suspended in formic acid (20 ml) followed by stirring at room temperature for several hours. After cooling to a temperature of from 0° to 5° C. in an ice-water bath, 30% hydrogen peroxide (1 ml) was added to the solution. The reaction was effected at a temperature of from 0° to 5° C. for 20 hours and, after the addition of 50 ml of water, the reaction mixture was extracted with chloroform. The extract was washed with water and then an aqueous sodium bicarbonate solution, dried over anhydrous sodium sulfate and evaporated. To the resulting oil was added 20 ml of 90% methanol containing 200 mg of potassium hydroxide followed by stirring at room temperature for one hour. The reaction mixture was extracted with diethyl ether and the extract was washed with water, dried over anhydrous sodium sulfate and evaporated. The oily residue was chromatographed on silica gel (20 g). Elution with chloroform containing 2–5% by volume of methanol gave 117.2 mg of purified 3α,24,25-trihydroxy-5β-cholestane. After crystallization from ethanol, the produce had a melting point of 152°–154° C.

I.R. spectrum (cm$^{-1}$, KBr): 3380(OH)

N.M.R. spectrum (δ in d$_6$-DMSO): 0.63(3H,S), 0.89(3H,S), 0.99(3H,S), 1.03(3H,S).

EXAMPLE 6

3α-Hydroxy-5β-cholest-24-ene (62.0 mg) was dissolved in 5 ml of dry diethyl ether and then osmium tetraoxide (4.48 mg) was added to the solution. The mixture was stirred at room temperature overnight and distilled to remove diethyl ether. To the residue were added 5 ml of ethanol, 2.5 ml of water and 300 mg of sodium bisulfite followed by refluxing for 2 hours. The black precipitate was removed by filtration and the filtrate was extracted with diethyl ether. The extract was washed with water, dried over anhydrous sodium sulfate and evaporated. The addition of a small amount of diethyl ether to the residue gave crystals. Recrystallization from ethanol gave 35 mg of 3α,24,25-trihydroxy-5β-cholestane.

The product did not show drop of mixed melting point with the product prepared in accordance with Example 5. Further, IR spectrum and NMR spectrum of the product were confirmed to be the same as those of the product of Example 5.

EXAMPLE 7

3α-Hydroxy-5β-cholest-24-ene (1.52 g) was dissolved in chloroform (10 ml) which had been purified by the distillation. To the solution was added 1.02 g of m-chloroperbenzoic acid and the mixture was allowed to stand overnight at 5° C. After the addition of 50 ml of chloroform, the mixture was washed with an aqueous ppotassium carbonate solution and then water, dried over anhydrous magnesium sulfate and evaporated. The oily residue was chromatographed on silica gel (50 g). Elution with chloroform gave 1.349 g of 3α-hydroxy-24,25-epoxy-5β-cholestane. H,b.S).

N.M.R. spectrum (δ in CCl$_4$): 0.64(3H,S), 0.91(3H,S), 1.20(3H,S), 1.23(3H,S), 3.50(1H,m), 4.12(1H,b.S9.

3α-Hydroxy-24,25-epoxy-5β-cholestane (808 mg) was dissolved in dry tetrahydrofuran (20 ml) and to the solution was added lithium aluminium hydride (0. g) and the mixture was refluxed mildly for 30 minutes. After cooling, a saturated aqueous sodium bicarbonate solution was slowly added to the mixture to decompose unreacted lithium aluminium hydride and, after the addition of 10% aqueous hydrochloric acid, and the reaction mixture was extracted with diethyl ether. The extract was washed with water, dried over magnesium sulfate and evaporated to give 612.6 mg of crystalline 3α,25-dihydroxy-5β-chloestane having a melting point of 184–185° C. after recrystallization from ethanol.

I.R. spectrum (cm⁻¹, KBr): 3340(OH).

Mass spectrum (m/e): 404(M+), 386.

N.M.R. spectrum (δ in CDCl₃): 0.64(3H,S), 0.92(6H,S), 1.20(3H,S), 3.60(1H,m).

What we claim is:

1. A steroid compound represented by the formula

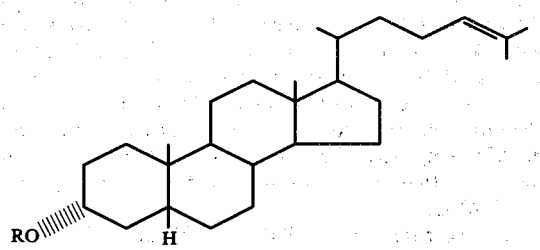

wherein R is hydrogen, acyl, triarylmethyl, methoxymethyl, tetrahydropyranyl or benzyl.

2. A steroid derivative according to claim 1 wherein R in the formula is hydrogen or acyl.

3. 3α-Hydroxy-5β-cholest-24-ene acetate according to claim 1.

4. 3α-Hydroxy-5β-cholest-24-ene according to claim 1.

5. A process for preparing a steroid derivative represented by the formula

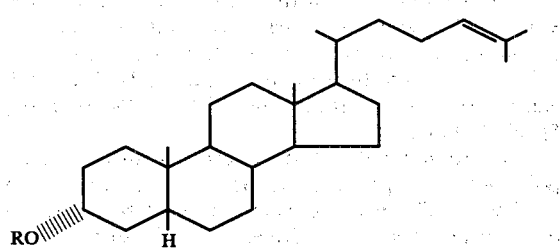

wherein R is hydrogen, acyl, triarylmethyl, methoxymethyl, tetrahydropyranyl or benzyl, which comprises reacting a compound represented by the formula wherein R' is acyl, triarylmethyl, methoxymethyl, tetrahydropyranyl or benzyl, with an acid or a halogenating agent and, optionally, hydrolizing the reaction product to remove the protective radical attached to the 3-hydroxyl radical.

6. A process according to claim 5 wherein said acid is sulfuric acid, p-toluenesulfonic acid or phosphoric anhydride.

7. A process according to claim 6 wherein the reaction is effected at a temperature ranging from room temperature to 200° C. for 1–24 hours.

8. A process according to claim 6 wherein the reaction is effected in an organic solvent selected from benzene, xylene, dimethylformamide, or toluene.

9. A processing according to claim 5 wherein said halogenating agent is phosphorus oxychloride, thionyl chloride, phosporus pentachloride or phosphorus trichloride.

10. A process according to claim 9 wherein the reaction using the halogenating agent is effected in the presence of a basic solvent selected from pyridine, triethylamine, dimethylamine or picoline.

11. A process according to claim 10 wherein the reaction is effected at a temperature ranging from room temperature to 200° C. for ½ to 24 hours.

12. A process according to claim 9 wherein the reaction is effected in a neutral solvent selected from benzene, chloroform or dichloromethane.

13. A process according to claim 12 wherein the reaction is effected at a temperature ranging from room temperature to 200° C. for ½ to 24 hours.

14. A process according to claim 12 wherein said reaction is effected in the presence of an inorganic base selected from sodium hydroxide of potassium hydroxide or an organic base selected from pyridine, triethylamine, collidine, dimethylaniline or picoline.

* * * * *

UNITED STATES PATENT AND TRADEMARK OFFICE
CERTIFICATE OF CORRECTION

PATENT NO. : 4,145,357
DATED : March 20, 1979
INVENTOR(S) : OCHI et al.

It is certified that error appears in the above-identified patent and that said Letters Patent are hereby corrected as shown below:

Title page, in the Abstract the formula should read

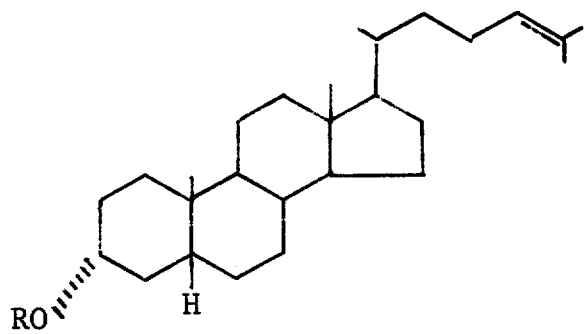

Column 5, line 11, that portion of the formula reading "-Dihydroxyss-" should read --Dihydroxy--

Signed and Sealed this

Twenty-eighth Day of August 1979

[SEAL]

Attest:

Attesting Officer

LUTRELLE F. PARKER
Acting Commissioner of Patents and Trademarks